United States Patent
Mistretta et al.

(10) Patent No.: US 7,711,166 B2
(45) Date of Patent: May 4, 2010

(54) HIGHLY CONSTRAINED RECONSTRUCTION OF MOTION ENCODED MR IMAGES

(75) Inventors: Charles A. Mistretta, Madison, WI (US); Julia Velikina, Madison, WI (US); Kevin Michael Johnson, Hartland, WI (US); Oliver Wieben, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 829 days.

(21) Appl. No.: 11/518,036

(22) Filed: Sep. 28, 2006

(65) Prior Publication Data

US 2007/0156044 A1   Jul. 5, 2007

Related U.S. Application Data

(60) Provisional application No. 60/780,788, filed on Mar. 9, 2006.

(51) Int. Cl.
   *G06K 9/00* (2006.01)
   *G01V 3/00* (2006.01)
   *A61B 5/05* (2006.01)

(52) U.S. Cl. .................. 382/128; 324/307; 600/410

(58) Field of Classification Search .............. 382/128, 382/129, 130, 131, 132, 133, 134; 378/4, 378/8, 9, 10, 15, 21, 23–27, 901; 600/407, 600/409, 410, 425, 524; 324/306, 307, 309; 128/920
See application file for complete search history.

(56) References Cited

U.S. PATENT DOCUMENTS

| | | | |
|---|---|---|---|
| 5,502,385 A | 3/1996 | Kuhn et al. | |
| 5,603,322 A * | 2/1997 | Jesmanowicz et al. | 600/410 |
| 5,604,778 A | 2/1997 | Polacin et al. | |
| 5,933,006 A * | 8/1999 | Rasche et al. | 324/307 |
| 6,490,472 B1 * | 12/2002 | Li et al. | 600/410 |
| 6,807,248 B2 | 10/2004 | Mihara et al. | |
| 6,954,067 B2 * | 10/2005 | Mistretta | 324/307 |
| 2001/0027262 A1 | 10/2001 | Mistretta et al. | |

FOREIGN PATENT DOCUMENTS

| | | |
|---|---|---|
| EP | 0 627 633 A1 | 7/1994 |
| WO | WO 2005/026765 | 3/2005 |

(Continued)

OTHER PUBLICATIONS

Wieslaw L. Nowinski, The Iterated Normalized Backprojection Method of Image Reconstruction, Institute of Computer Science, Polish Academy of Sciences Ordona 21, 01-237 Warsaw, Poland.

(Continued)

*Primary Examiner*—Abolfazl Tabatabai
(74) *Attorney, Agent, or Firm*—Quarles & Brady LLP

(57) ABSTRACT

A series of velocity encoded MR image frames are acquired. To increase the temporal resolution of the acquired image frames radial projections are acquired and each image frame is highly undersampled. The radial projections for each velocity encoding direction are interleaved throughout the scan and a composite phase image is reconstructed from these and used to reconstruct a velocity image for each image frame in a highly constrained backprojection method.

19 Claims, 12 Drawing Sheets

FOREIGN PATENT DOCUMENTS

WO  WO 2005/069031  7/2005

OTHER PUBLICATIONS

Y. Huang et al, Time-Resolved 3D MR Angiography by Interleaved Biplane Projection, Proc. Intl. Soc. Mag. Reson. Med. 13 (2005).

T.A. Cashen et al, Comparison of Temporal and Spatial Undersampling Techniques for Time-Resolved Contrast-Enhanced MR Angiography, Proc. Intl. Soc. Mag. Reson. Med. 13, (2005).

Graeme C. McKinnon et al, Towards Imaging the Beating Heart Usefully with a Conventional CT Scanner, Trans. on Biomedical Eng., vol. BME-28, No. 2, p. 123-127, Feb. 1981.

Kathryn L. Garden et al, 3-D Reconstruction of the Heart from few Projections: A Practical Implementation of the McKinnon-Bates Algorithm, Trans. on Biomedical Eng., vol. MI-5, No. 4, p. 233-234, Dec. 1986.

A.L. Wentland et al, Technique for Acquiring MR Images of CSF Flow During a Valsalva Maneuver, Med. Phys. Univ. of WI, Madison WI.

K.M. Johnson et al, Average and Time-Resolved Dual Velocity Encoded Phase Contrast Vastly Undersampled Isotropic Projection Imaging, Med. Phys. Univ. of WI, Madison WI.

K.M. Johnson et al, Transtenotic Pressure Gradient Measurements Using Phase Contrast Vastly Undersampled Isotropic Projection Imaging (PC-VIPR) in a Canin Model, Med. Phys. Univ. of WI, Madison WI.

C.A. Mistretta et al, Highly Constrained Backprojection for Time-Resolved MRI, Mag. Reson. Med. 55:30-40 (2006).

Zhi-Pei Liang et al, Constrained Reconstruction Methods in MR Imaging, Reviews of Mag. Reson. in Med. vol. 4, pp. 67-185, 1992.

J.G. Pipe et al, Spiral Projection Imaging: a new fast 3D trajectory, Proc. Intl. Soc. Mag. Reson. Med. 13, (2005).

K.V. Koladia et al, Rapid 3D PC-MRA using Spiral Projection Imaging, Proc. Intl. Soc. Mag. Reson. Med. 13, (2005).

J. Tsao et al, k-t BLAST and k-t SENSE: Dynamic MRI With High Frame Rate Exploiting Spatiotemporal Correlations, Mag. Reson. Med. 50:1031-1042 (2003).

Zhi-Pei Liang et al, Constrained Imaging-Overcoming the Limitations of the Fourier Series, IEEE Engineering in Medicine and Biology, Sep./Oct. 1996, pp. 126-132.

Zhi-Pei Liang et al, Fast Algorithm for GS-Model-Based Image Reconstruction in Data-Sharing Fourier Imaging, IEEE Transactions on Med. Imaging, vol. 22, No. 8, pp. 1026-1030, Aug. 2003.

Klass P. Pruessmann et al, Advances in Sensitivity Encoding With Arbitrary k-Space Trajectories, Mag. Reson. in Med. 46:638-651 (2001).

R. Fahrig et al, Use of a C-Arm System to Generate True Three-dimensional Computed Rotational Angiograms: Preliminary In Vitro and In Vivo Results, AJNR: 18, pp. 1507-1514,Sep. 1997.

A.V. Barger, et al, Single Breath-Hold 3D Contrast-Enhanced Method for Assessment of Cardiac Function, Mag. Reson. in Med. 44:821-824 (2000).

J. Du et al, Time-Resolved Undersampled Projection Reconstruction Imaging for High-Resolution CE-MRA of the Distal Runoff Vessels, Mag. Reson. in Med. 48:516-522 (2002).

Ashwani Aggarwal et al, Imaging in Turbid Media by Modified Filtered Back Projection Method Using Data From Monte Carlo Simulation, Proc. of SPIE vol. 5047, pp. 314-324.

Xavier Golay, et al, Presto-Sense: An Ultrafast Whole-Brain fMRI Technique, Mag. Reson. in Med. 43:779-786 (2000).

Ronald R. Price, et al, Practical Aspects of Functional MRI (NMR Task Group #6), Medical Physics, vol. 29, No. 8, pp. 1892-1912, Aug. 2002.

M.S. Hansen et al, k-t Blast Reconstruction From Arbitrary k-t space Sampling: Application to Dynamic Radial Imaging, Proc. Intl. Soc. Mag. Reson. Med. 13 p. 684 (2005).

* cited by examiner

HIGHLY CONSTRAINED RECONSTRUCTION OF MOTION ENCODED MR IMAGES

CROSS-REFERENCE TO RELATED APPLICATIONS

This application claims the benefit of U.S. Provisional patent application Ser. No. 60/719,445 filed on Sep. 22, 2005 and entitled "Highly Constrained Image Reconstruction Method" and U.S. Provisional patent application Ser. No. 60/780,788 filed on Mar. 9, 2006 and entitled "Highly Constrained Reconstruction Of velocity Encoded MR Images".

STATEMENT REGARDING FEDERALLY SPONSORED RESEARCH

This invention was made with government support under Grant Nos. HL 072260 and LH 066488 awarded by the National Institute of Health. The United States Government has certain rights in this invention.

BACKGROUND OF THE INVENTION

The field of the invention is magnetic resonance imaging ("MRI") methods and systems. More particularly, the invention relates to the acquisition and reconstruction of MR images with pulse sequences that employ gradients indicative of motion.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

The prevailing methods used to acquire NMR signals and reconstruct images use a variant of the well known Fourier transform (FT) imaging technique. This technique is discussed in an article entitled "Spin-Warp NMR Imaging and Applications to Human Whole-Body Imaging" by W. A. Edelstein et al., *Physics in Medicine and Biology*, Vol. 25, pp. 751-756 (1980). It employs a variable amplitude phase encoding magnetic field gradient pulse prior to the acquisition of NMR spin-echo signals to phase encode spatial information in the direction of this gradient. In a two-dimensional implementation (2DFT), for example, spatial information is encoded in one direction by applying a phase encoding gradient ($G_y$) along that direction, and then a spin-echo signal is acquired in the presence of a readout magnetic field gradient ($G_x$) in a direction orthogonal to the phase encoding direction. The readout gradient present during the spin-echo acquisition encodes spatial information in the orthogonal direction. In a typical 2DFT pulse sequence, the magnitude of the phase encoding gradient pulse $G_y$ is incremented ($\Delta G_y$) in the sequence of views that are acquired during the scan to produce a set of NMR data from which an entire image can be reconstructed. With this method Fourier space, or "k-space", is sampled along Cartesian coordinates in a scanning pattern such as that shown in FIG. 2A.

To increase the rate at which an image is acquired, image quality may be sacrificed by acquiring fewer phase encoding views, or by using faster pulse sequences that inherently result in lower quality images. With the Fourier transform methods, therefore, there is a trade-off between the number of views that are acquired to achieve the desired image resolution and quality, and the rate at which NMR data for a complete image may be acquired.

MR methods have been developed that encode spin motion into the phase of the acquired signal as disclosed in U.S. Pat. No. Re. 32,701. These form a class of techniques known as phase contrast (PC) methods. Currently, most PC techniques acquire two images, with each image having a different sensitivity to the same velocity component. Images may then be produced by forming either the phase difference or complex difference between the pair of velocity-encoded images. This motion encoding method is used to image flowing blood in what is commonly referred to as phase contrast magnetic resonance angiography (PCMRA).

Phase contrast techniques have also been used to image flow and provide quantitative measurement of blood flow. In flow imaging the motion encoding gradients used during the scan are sensitive to velocity components in two or three orthogonal directions. From the resulting velocity component images, total quantitative flow images can be produced. However, the scan becomes unduly long when four to six fully sampled images must be acquired using different motion encoding gradients.

As described in U.S. Pat. No. 6,188,922 the acquisition of velocity encoded MR data can be shortened by sampling k-space with a series of interleaved projection views. Projection views sample k-space along radial trajectories and it was discovered that far fewer projection views are required to produce a quality image than with phase encoded views that sample k-space along Cartesian coordinates. Such a radial sampling pattern is shown in FIG. 2B.

There are two methods used to reconstruct images from an acquired set of projection views as described, for example, in U.S. Pat. No. 6,710,686. In MRI the most common method is to regrid the k-space samples from their locations on the radial sampling trajectories to a Cartesian grid. The image is then reconstructed by performing a 2D or 3D Fourier transformation of the regridded k-space samples. The second method for reconstructing an MR image is to transform the radial k-space projection views to Radon space by first Fourier transforming each projection view. An image is reconstructed from these signal projections by filtering and backprojecting them into the field of view (FOV). As is well known in the art, if the acquired signal projections are insufficient in number to satisfy the Nyquist sampling theorem, streak artifacts are produced in the reconstructed image.

The standard backprojection method used in MRI is shown in FIG. 3. Each acquired signal projection profile 110 is Fourier transformed and then backprojected onto the field of view 12 by projecting each signal sample 14 in the transformed profile 10 through the FOV 12 along the projection path as indicted by arrows 16. In projecting each signal sample 16 in the FOV 12 we have no a priori knowledge of the subject being imaged and the assumption is made that the NMR signals in the FOV 12 are homogeneous and that the signal sample 14 should be distributed equally in each pixel through which the projection path passes. For example, a projection path 8 is illustrated in FIG. 3 for a single signal sample 14 in one transformed signal projection profile 10 as it passes through N pixels in the FOV 12. The signal value (P) of this signal sample 14 is divided up equally between these N pixels:

$$S_n = (P \times 1)/N \quad (1)$$

where: $S_n$ is the signal value distributed to the $n^{th}$ pixel in a projection path 8 having N pixels.

Clearly, the assumption that the backprojected signal in the FOV 12 is homogeneous is not correct. However, as is well known in the art, if certain corrections are made to each signal profile 10 and a sufficient number of profiles are acquired at a corresponding number of projection view angles, the errors caused by this faulty assumption are minimized and image artifacts are suppressed. In a typical, filtered backprojection method of image reconstruction, 400 projections are required for a 256×256 pixel 2D image and 103,000 projections are required for a 256×256×256 voxel 3D image.

SUMMARY OF THE INVENTION

The present invention is a method for reconstructing an image from acquired velocity encoded MR data, and more particularly, a highly constrained backprojection method that enables a velocity encoded image to be reconstructed from a highly undersampled data set. By using the highly constrained backprojection method of the present invention, a velocity encoded image can be acquired with far fewer views and without producing clinically objectionable image artifacts due to undersampling. This reduces the acquisition time and enables images to be acquired at different velocity encodings.

A discovery of the present invention is that good quality images can be produced with far fewer projection signal profiles 10 if a priori knowledge of the signal contour in the FOV 12 is used in the reconstruction process. A composite image is acquired as part of the MRI scan, and it is reconstructed to provide a priori knowledge of the subject being imaged. This composite image is used during the reconstruction of highly under sampled velocity encoded images to weight the distribution of backprojected views. Referring to FIG. 4, for example, the signal contour in the FOV 12 may be known to include structures 18 and 20. That being the case, when the backprojection path 8 passes through these structures a more accurate distribution of the signal sample 14 in each pixel is achieved by weighting the distribution as a function of the known signal contour at that pixel location. As a result, a majority of the signal sample 14 will be distributed in the example of FIG. 4 at the pixels that intersect the structures 18 and 20. For a backprojection path 8 having N pixels this highly constrained backprojection may be expressed as follows:

$$S_n = (P \times C_n) \bigg/ \sum_{n=1}^{N} C_n \quad (2)$$

where: $S_n$=the backprojected signal magnitude at a pixel n in an image being reconstructed;

P=the backprojected signal sample value in the transformed projection profile; and $C_n$=signal value of an a priori composite image at the $n^{th}$ pixel along the backprojection path.

The composite image is reconstructed from data acquired during the scan, and may include that used to reconstruct the image as well as other acquired image data that depicts the structure in the field of view. The numerator in equation (2) weights each pixel using the corresponding signal value in the composite image and the denominator normalizes the value so that all backprojected signal samples reflect the projection sums for the image frame and are not multiplied by the sum of the composite image. It should be noted that while the normalization can be performed on each pixel separately after the backprojection, in many clinical applications it is far easier to normalize the projection P before the backprojection. In this case, the projection P is normalized by dividing by the corresponding value $P_c$ in a projection through the composite image at the same view angle. The normalized projections $P/P_c$ are backprojected and the resulting image is then multiplied by the composite image.

A 3D embodiment is shown graphically in FIG. 5 for a single 3D projection view characterized by the view angles θ and φ. This projection view is back projected along axis 16 and spread into a Radon plane 21 at a distance r along the back projection axis 16. Instead of a filtered back projection in which projection signal values are filtered and uniformly distributed into the successive Radon planes, along axis 16, the projection signal values are distributed in the Radon plane 22 using the information in the composite image. The composite image in the example of FIG. 5 contains structures 18 and 20. The weighted signal contour value is deposited at image location x, y, z in the Radon plane 21 based on the intensity at the corresponding location x, y, z in the composite image. This is a simple multiplication of the signal profile value by the corresponding composite image voxel value. This product is then normalized by dividing the product by the profile value from the corresponding image space profile formed from the composite image. The formula for the 3D reconstruction is $$I(x, y, z) = \Sigma(P(r, \theta, \phi) * C(x, y, z)_{(r,\theta,\phi)} / P_c(r, \theta, \phi)) \quad (2a)$$

where the sum (Σ) is over all projections in the image frame being reconstructed and the x, y, z values in a particular Radon plane are calculated using the profile value P(r,θ,φ) at the appropriate r,θ,φ value for that plane. $P_c(r,\theta,\phi)$ is the corresponding profile value from the composite image, and C(x, y, z)$_{r,\theta,\phi}$ is the composite image value at (r,θ,φ).

An object of the invention is to shorten the scan time needed to acquire a phase contrast magnetic resonance angiography (PCMRA) image. The present invention enables a substantial reduction in the number of views needed to acquire a PCMRA image when a series of such images are to be acquired.

Another object of the invention is to shorten the scan time needed to acquire velocity or flow images without loosing the quantitative measurement capability. One of the problems in reconstructing velocity images using this highly constrained backprojection method is that the velocity at any image pixel can have either a positive or negative value depending on the direction of spin motion at that pixel location. As a result, when a projection view is acquired the projection ray may pass through pixels having both positive and negative velocity values. Indeed, it is even possible that the total velocity along any projection ray may sum to zero. To avoid problems this can present it is a teaching of the present invention that all signals are treated as absolute values during the highly constrained backprojection process and the signs of the processed signals are then restored in the reconstructed images.

Yet another object of the invention is to produce a complex difference image using a highly constrained backprojection method. This is achieved by separately reconstructing I component and Q component images using the highly constrained backprojection method and then combining the resulting I component and Q component images.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

Figure 1:
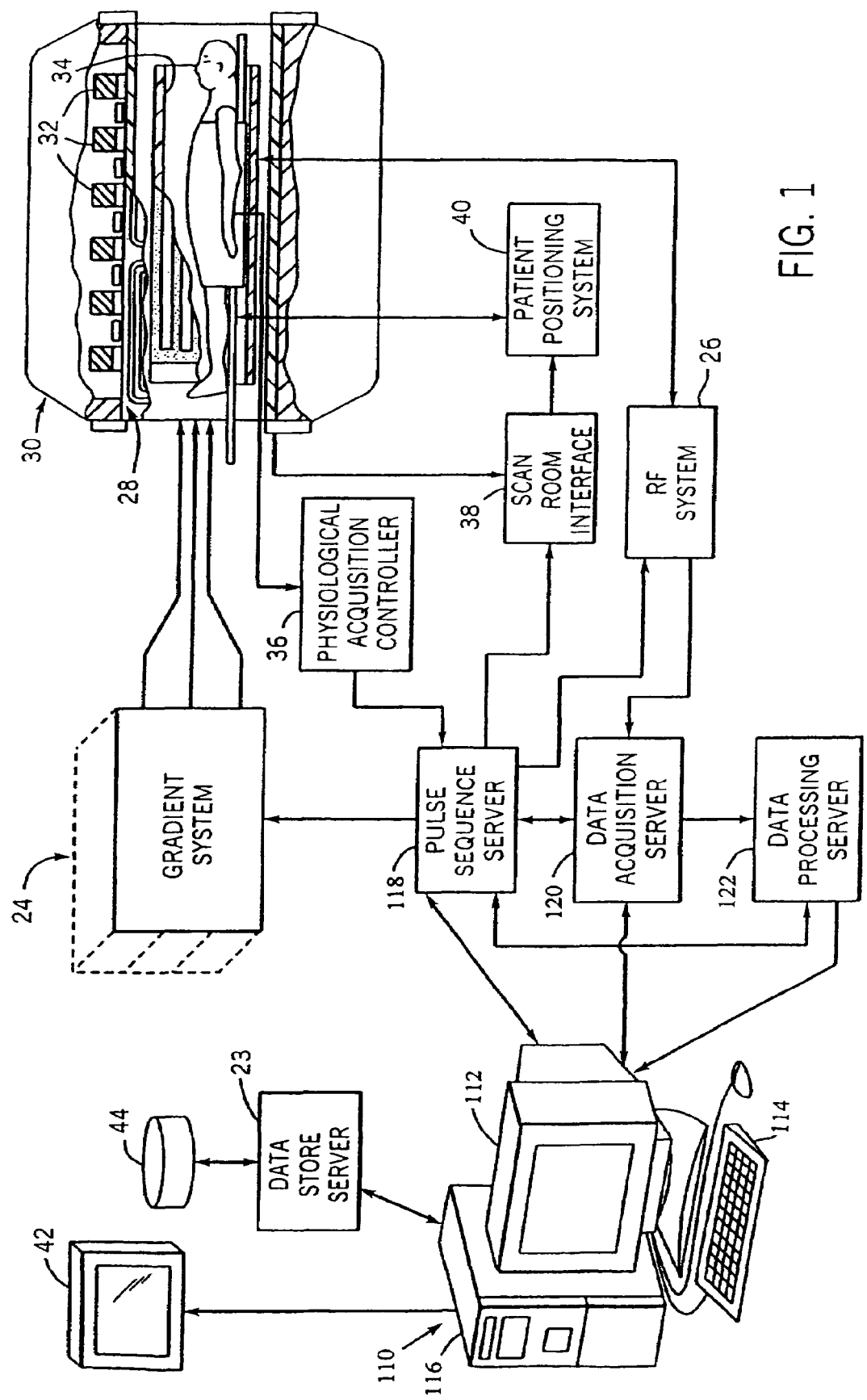
FIG. 1 is a block diagram of an MRI system used in the preferred embodiment of the invention.
Figure 2A:
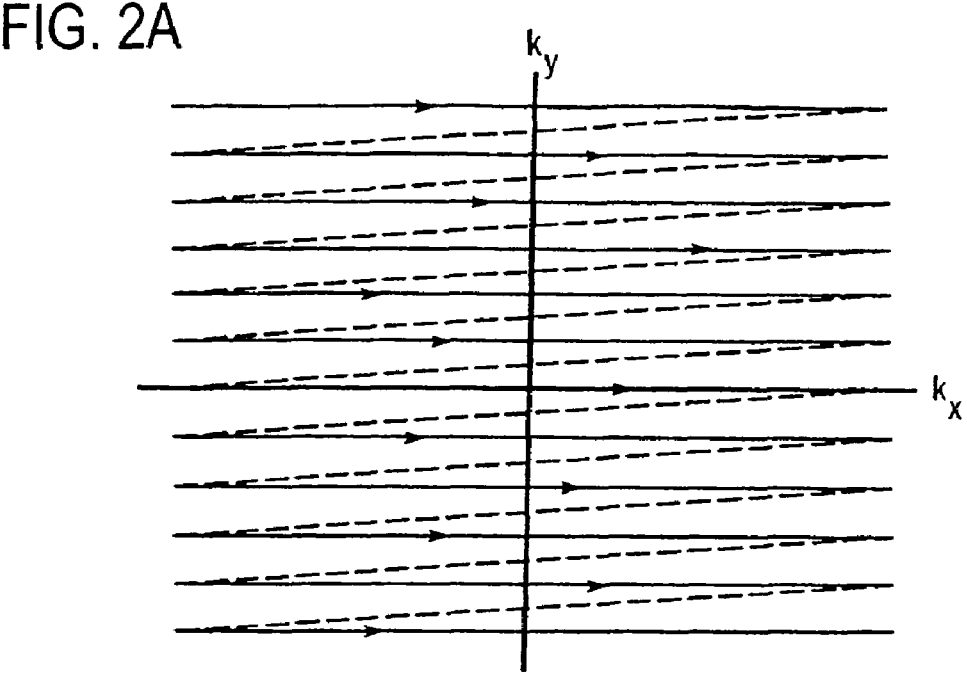
FIG. 2A is a graphic illustration of the manner in which k-space is sampled during a typical Fourier, or spin-warp, image acquisition using an MRI system.
Figure 2B:
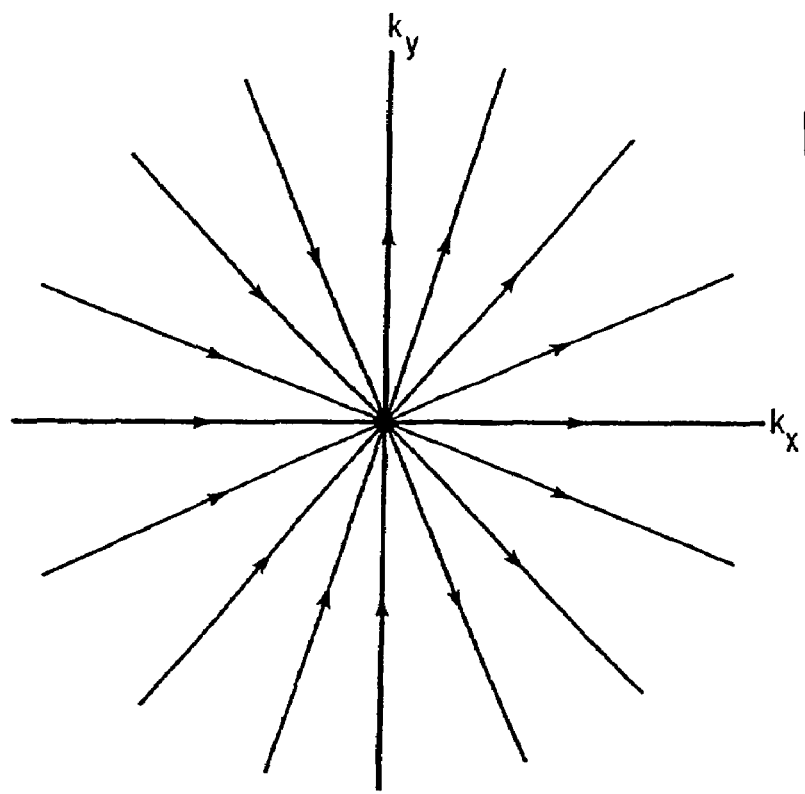
FIG. 2B is a graphic illustration of the manner in which k-space is sampled during a typical projection reconstruction image acquisition using an MRI system.
Figure 3:
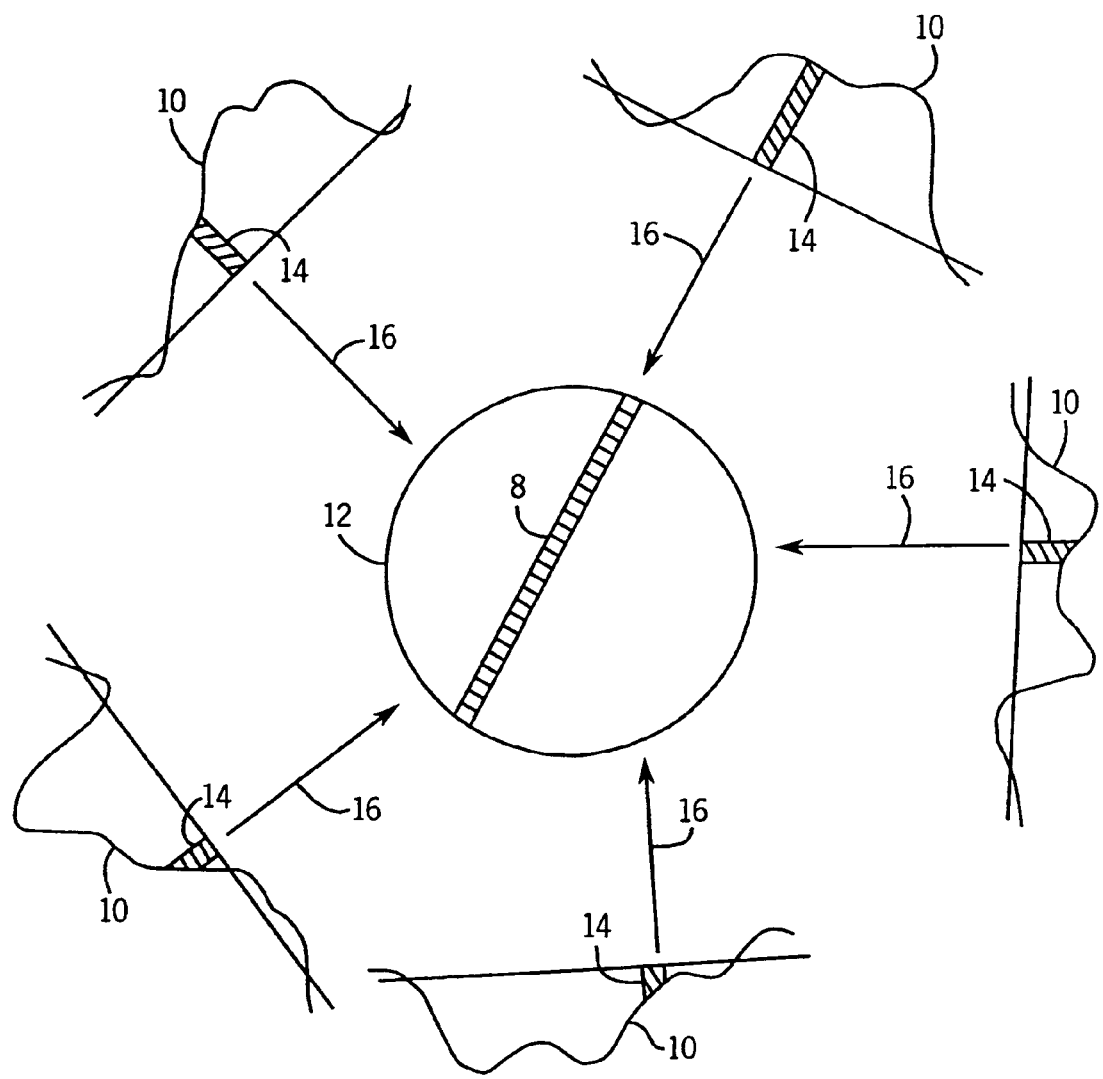
FIG. 3 is a pictorial representation of a conventional backprojection step in an image reconstruction process.

Referring particularly to FIG. 1, the preferred embodiment of the invention is employed in an MRI system. The MRI system includes a workstation 110 having a display 112 and a keyboard 114. The workstation 110 includes a processor 116 which is a commercially available programmable machine running a commercially available operating system. The workstation 110 provides the operator interface which enables scan prescriptions to be entered into the MRI system.

The workstation 110 is coupled to four servers: a pulse sequence server 118; a data acquisition server 120; a data processing server 122, and a data store server 23. In the preferred embodiment the data store server 23 is performed by the workstation processor 116 and associated disc drive interface circuitry. The remaining three servers 118, 120 and 122 are performed by separate processors mounted in a single enclosure and interconnected using a 64-bit backplane bus. The pulse sequence server 118 employs a commercially available microprocessor and a commercially available quad communication controller. The data acquisition server 120 and data processing server 122 both employ the same commercially available microprocessor and the data processing server 122 further includes one or more array processors based on commercially available parallel vector processors.

The workstation 110 and each processor for the servers 118, 120 and 122 are connected to a serial communications network. This serial network conveys data that is downloaded to the servers 118, 120 and 122 from the workstation 110 and it conveys tag data that is communicated between the servers and between the workstation and the servers. In addition, a high speed data link is provided between the data processing server 122 and the workstation 110 in order to convey image data to the data store server 23.

The pulse sequence server 118 functions in response to program elements downloaded from the workstation 110 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$ and G, used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 118. The RF system 26 includes an RF transmitter for producing a wide variety of RF pulses used in MR pulse sequences. The RF transmitter is responsive to the scan prescription and direction from the pulse sequence server 118 to produce RF-pulses of the desired frequency, phase and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2+Q^2}, \tag{3}$$

and the phase of the received NMR signal may also be determined:

$$\phi=\tan^{-1} Q/I. \tag{4}$$

The pulse sequence server 118 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 118 to synchronize, or "gate", the performance of the scan with the subject's respiration or heart beat.

The pulse sequence server 118 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

It should be apparent that the pulse sequence server 118 performs real-time control of MRI system elements during a scan. As a result, it is necessary that its hardware elements be operated with program instructions that are executed in a timely manner by run-time programs. The description components for a scan prescription are downloaded from the workstation 110 in the form of objects. The pulse sequence server 118 contains programs which receive these objects and converts them to objects that are employed by the run-time programs.

The digitized NMR signal samples produced by the RF system 26 are received by the data acquisition server 120. The data acquisition server 120 operates in response to description components downloaded from the workstation 110 to receive the real-time NMR data and provide buffer storage such that no data is lost by data overrun. In some scans the data acquisition server 120 does little more than pass the acquired NMR data to the data processor server 122. However, in scans which require information derived from acquired NMR data to control the further performance of the scan, the data acquisition server 120 is programmed to produce such information and convey it to the pulse sequence server 118. For example, during prescans NMR data is acquired and used to calibrate the pulse sequence performed by the pulse sequence server 118. Also, navigator signals may be acquired during a scan and used to adjust RF or gradient system operating parameters or to control the view order in which k-space is sampled. And, the data acquisition server 120 may be employed to process NMR signals used to detect the arrival of contrast agent in an MRA scan. In all these examples the data acquisition server 120 acquires NMR data and processes it in real-time to produce information which is used to control the scan.

The data processing server 122 receives NMR data from the data acquisition server 120 and processes it in accordance with description components downloaded from the workstation 110. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc.

Images reconstructed by the data processing server 122 are conveyed back to the workstation 110 where they are stored. Real-time images are stored in a data base memory cache (not shown) from which they may be output to operator display 112 or a display 42 which is located near the magnet assembly 30 for use by attending physicians. Batch mode images or selected real time images are stored in a host database on disc storage 44. When such images have been reconstructed and transferred to storage, the data processing server 122 notifies the data store server 23 on the workstation 110. The workstation 110 may be used by an operator to archive the images, produce films, or send the images via a network to other facilities.

Two embodiments of the invention are described below which employ the MRI system of FIG. 1. The first embodiment provides a velocity image which quantitatively indicates the total spin velocity at each image pixel. The second embodiment produces a PCMRA image in which the motion encoding gradient provides a phase contrast mechanism for imaging moving blood.

Figure 6:
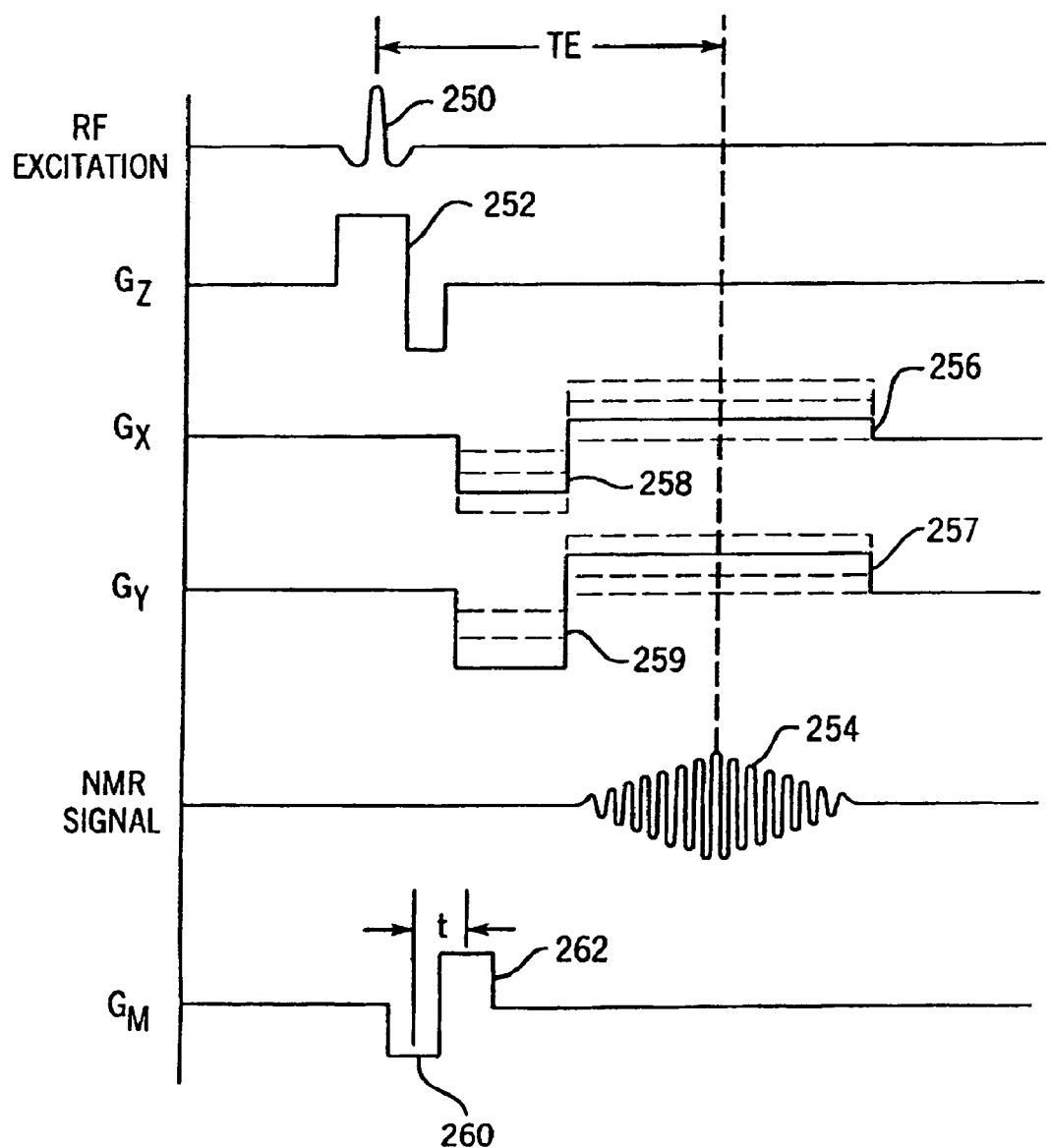
FIG. 6 is a preferred 2D pulse sequence used by the MRI system of FIG. 1 to practice the present invention.

Referring particularly to FIG. 6, an exemplary motion encoded pulse sequence performed by the pulse sequence server 118 is a gradient-recalled echo pulse sequence in which an RF excitation pulse 250 is applied in the presence of a $G_z$ slice select gradient 252, and an NMR echo signal 254 is acquired in the presence of $G_x$ and $G_y$ readout gradients 256 and 257. Each readout gradient 256 and 257 is preceded by a dephasing gradient 258 and 259 respectively which dephases the transverse magnetization produced by RF excitation pulse 250. The readout gradients 256 and 257 rephase the spin magnetization at the echo time TE to produce the peak in the NMR echo signal 254.

Figure 8:
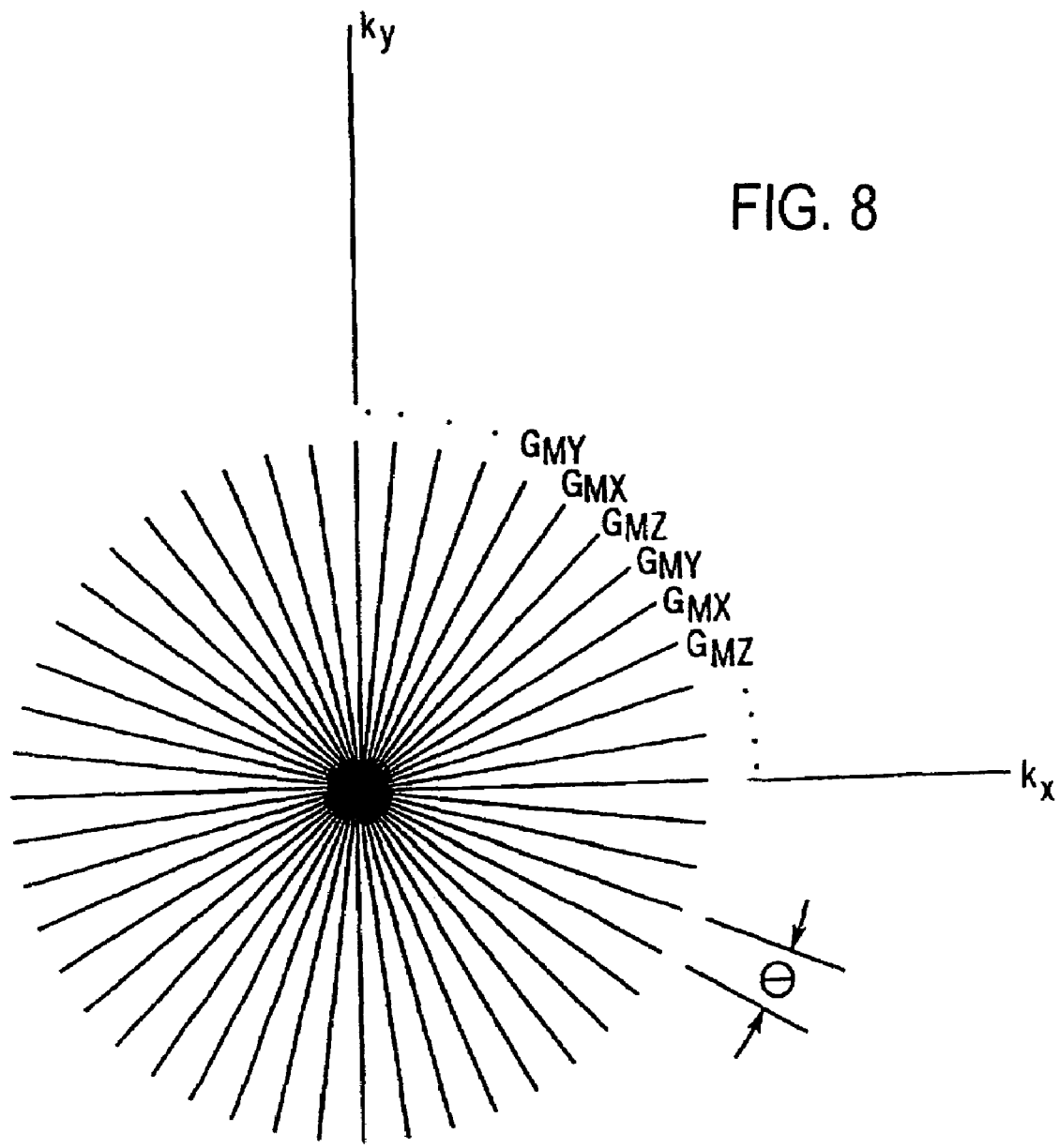
FIG. 8 is a pictorial representation of the sampling of k-space which occurs while practicing a preferred embodiment of the invention.

With no motion encoding gradients used, this pulse sequence is repeated and the magnitudes of the two readout gradients 256 and 257 are stepped to different values to acquire the NMR echo signal 254 at different projection angles. This is illustrated in FIG. 8, where each radial line represents the sampling of $k_x$-$k_y$ space accomplished by each acquired NMR echo signal 254. The amplitudes of the readout gradients 256 and 257 and the amplitudes of their corresponding dephasing gradient pulses 258 and 259 are stepped through values such that each successive projection is rotated by an angle θ.

Referring again to FIG. 6, to produce a motion encoded MR image, each acquired projection is velocity sensitized by a bipolar motion encoding gradient $G_M$. As is well known in the art, a velocity encoding gradient $G_M$ is comprised of two gradient lobes 260 and 262 of equal size and opposite polarity. The motion encoding gradient $G_M$ can be applied in any direction and it is played out after transverse magnetization is produced by the RF excitation pulse 250 and before the NMR echo signal 254 is acquired. The motion encoding gradient $G_M$ imposes a phase shift to the NMR signals produced by spins moving in the direction of the gradient $G_M$ and the amount of this phase shift is determined by the velocity of the moving spins and the first moment of the motion encoding gradient $G_M$. The first moment ($M_1$) is equal to the product of the area of gradient pulse 260 or 262 and the time interval (t) between them. The first moment $M_1$ is set to provide a significant phase shift, but not so large as to cause the phase to wrap around at high spin velocities.

To ensure that phase shifts in the acquired NMR signals 254 are due solely to spin motion, a reference acquisition is usually made at each projection angle. In the preferred embodiment, for each motion encoded projection view acquired with a motion encoding gradient $G_M$ having a first moment $M_1$, a second projection view having the same motion encoding gradient $G_M$ with a negative first moment $-M_1$ is acquired. This is achieved by simply reversing the polarity of the two $G_M$ gradient lobes 260 and 262. As will be explained below, when the two resulting signals are subtracted, the phase shifts not due to spin motion are removed from the velocity determination. These undesired phase shifts are referred to below as the background phase $\phi_B$.

As indicated above, the motion encoding gradient $G_M$ can be applied in any direction. In the preferred embodiment, the motion encoding gradient $G_M$ is applied separately along each of the gradient axes, x, y and z such that an image indicative of total spin velocity can be produced. That is, an image indicative of velocity along the z axis ($v_z$) is produced by acquiring an image with the bipolar motion encoding gradient $G_M$ added to the $G_z$ gradient waveform shown in FIG. 6, a second velocity image $V_x$ is acquired with the motion encoding gradient $G_M$ added to the $G_x$ gradient waveform, and a third velocity image $V_y$ is acquired with the motion encoding gradient $G_M$ added to the $G_y$ gradient waveform. An image indicative of the total spin velocity is then produced by combining the corresponding pixel values in the three velocity images $$V_T = \sqrt{V_x^2 + V_y^2 + V_z^2} \tag{5}$$

While it is possible to acquire the motion encoded NMR echo signals 254 at each projection angle θ to fully sample k-space, in this embodiment the different motion encoding directions are acquired at different, interleaved projection angles. This is illustrated in FIG. 8 where $G_{MX}$ indicates projections acquired with the motion encoding gradient directed along the x axis, $G_{MY}$ indicates projections acquired with the motion encoding gradient directed along the y axis, and $G_{MZ}$ indicates projections acquired with the motion encoding gradient directed along the z axis. A total of m=10 different projections are acquired for each of the three motion encoding directions and these are spaced apart at equal angles of 3θ. Each set of the acquired projections is interleaved with the projections acquired for the other two directions with the result that all projection views for an image frame are spaced apart at equal angles θ to sample k-space in a substantially uniform manner.

Figure 9:
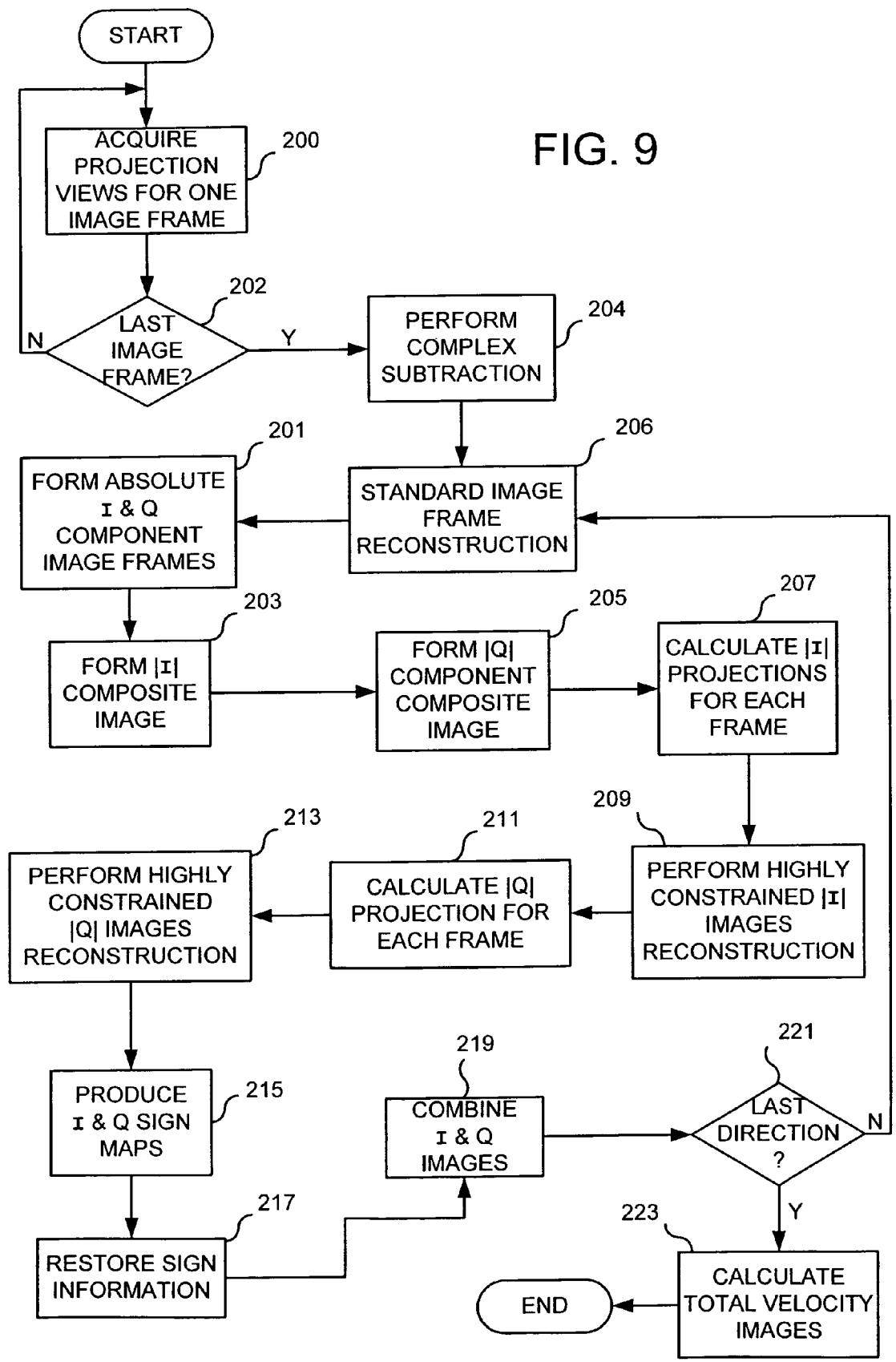
FIG. 9 is a flow chart of the steps used by the MRI system of FIG. 1 to practice a preferred embodiment of the invention.

Referring particularly to FIG. 9, in the first preferred embodiment of the invention the above-described 2D pulse sequence is employed to acquire a series of image frames from which corresponding velocity images may be reconstructed. As indicated at process block 200, the pulse sequence is performed by the MRI system to acquire a set (m=10) of motion encoded NMR signals for each of the x, y and z directions. These projection views are equally spaced to sample k-space as uniformly as possible and the different motion encoding directions are interleaved as shown in FIG. 8. Image frames are continuously and quickly acquired in this manner until the prescribed number of image frames (n) have been acquired as determined at decision block 202.

Figure 7:
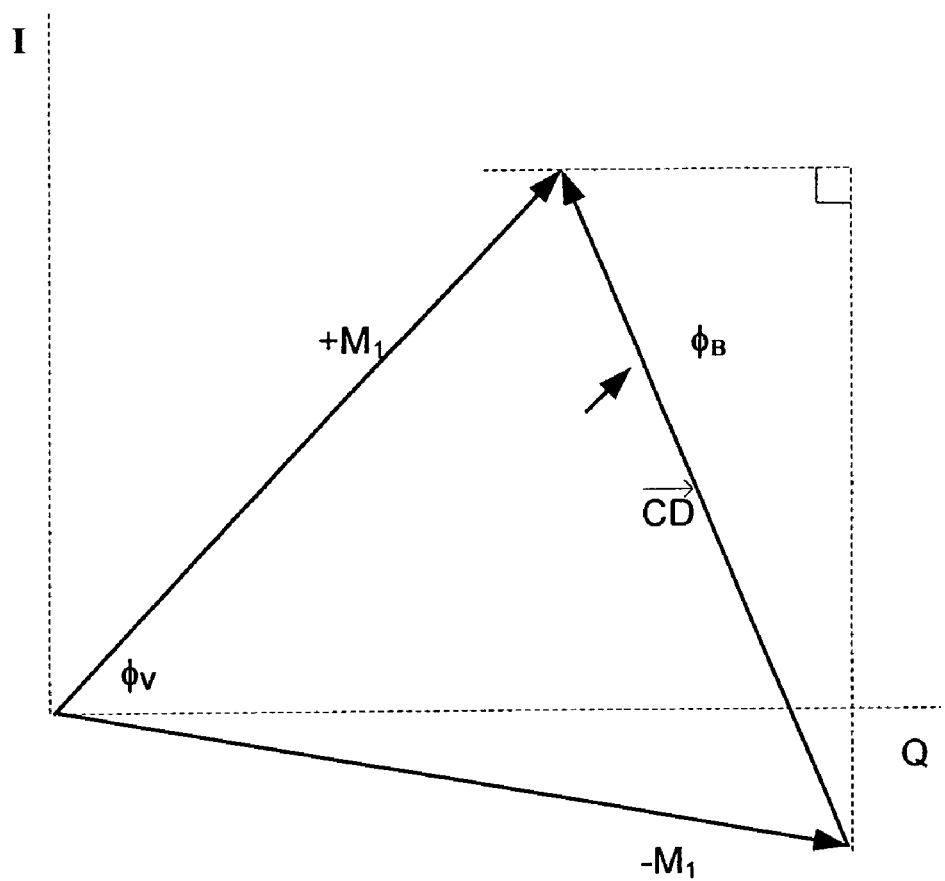
FIG. 7 is a vector diagram of signal components.
Figure 11:
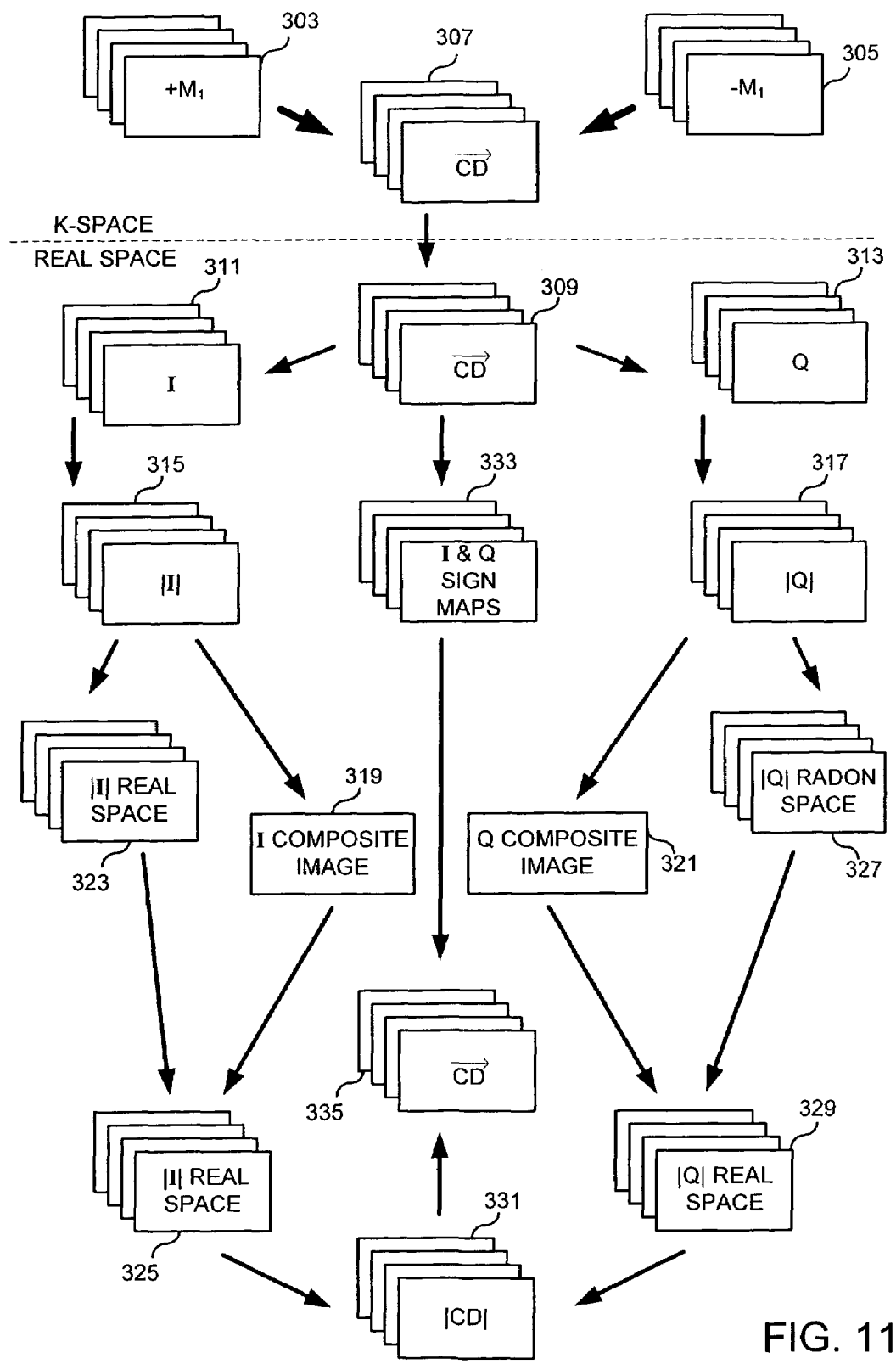
FIG. 11 is a flow chart of the data structures produced according to the method of FIG. 9.

In this embodiment of the invention the image reconstruction is performed after the data acquisition phase of the scan is complete. This reconstruction process may be performed on the data processing server 122, or the acquired data may be off-loaded to a separate work station to free up the MRI system. Referring still to FIG. 9, the first step in the image reconstruction process is to perform a complex subtraction of each ±$M_1$ pair of projections for each motion encoded direction as indicated at process block 204. Referring also to FIG. 11, this is a subtraction of the respective I and Q components of corresponding signal samples in the +$M_1$ and −$M_1$ projection data sets 303 and 305 to produce a complex difference ($\vec{CD}$) projection data set 307. This complex difference vector $\vec{CD}$ is shown in FIG. 7. This is done for all n of the acquired image frames and then, as indicated at process block 206, image frames are reconstructed from each set of complex difference projections $\vec{CD}$ 307 to produce corresponding real space complex difference images 309. This is a standard reconstruction and in the preferred embodiment this reconstruction includes regridding the k-space samples in the ten $\vec{CD}$ projections into Cartesian coordinates and then performing a 2D complex, inverse Fourier transformation. It can be appreciated however that these images can also be reconstructed using a conventional filtered backprojection method after converting the $\vec{CD}$ projections to Radon space with a 1DFT. In either case, because k-space is highly undersampled, these images will be of very poor quality from a clinical standpoint. However, they do retain the vector nature of the complex difference $\vec{CD}$ at each pixel, and in particular, the direction of that vector. As will become apparent from the discussion below, this "sign" information will be restored to absolute value images of much higher quality.

The next step as indicated at process block 201 is to separate the I and Q components at each $\vec{CD}$ image frame pixel to form separate $\vec{I}$ and $\vec{Q}$ image frames 311 and 313. And then, the absolute value of the $\vec{I}$ and $\vec{Q}$ components in these image frames are taken to form corresponding absolute image frames |I| and |Q| 315 and 317. These image frames can be viewed collectively as phase images that indicate spin "speed", since they preserve the phase shifts produced by spin motion, but not the direction. The direction, or sign, information is lost in these absolute value images.

As indicated at process block 203, a composite image 319 for the |I| component is then formed. This is achieved by adding the corresponding |I| pixel values together for all n image frames 315. As indicated above, the projection views acquired for the n image frames are interleaved with each other with the result that the |I| composite image 319 has a much higher quality than any one of the absolute image frames |I| 315. As indicated at process block 205, this procedure is repeated with the |Q| component images 317 to also form a |Q| composite image 321. Collectively these |I| and |Q| composite images 319 and 321 can be viewed as composite phase images since they preserve the phase information and hence speed.

As indicated at process block 207, the next step is to produce a set of |I| component projections 323 for each of the n |I| component image frames 315. This is a standard Radon transformation in which 10 projections (in this preferred embodiment) are produced at the same view angles used to acquire the image frame. This is done using the Radon transformation tool in the commercially available software sold under the trademark "MATLAB" by Mathworks, Inc. We thus have a set of 10 projections for each of the n image frames 315 for the |I| component of the complex difference.

A highly constrained image reconstruction process is then performed as indicated at process block 209 to produce n high quality |I| component images 325 from these sets of Radon space projections 323. This reconstruction method uses the |I| component composite image 319 as will be described in more detail below with reference to FIG. 10.

As indicated at process blocks 211 and 213 the above steps are then repeated for the |Q| component. A set of |Q| component projections 327 are calculated for each image frame 317 using a Radon transformation and then n |Q| component image frames 329 are reconstructed using the highly constrained backprojection method which will now be described.

Figure 4:
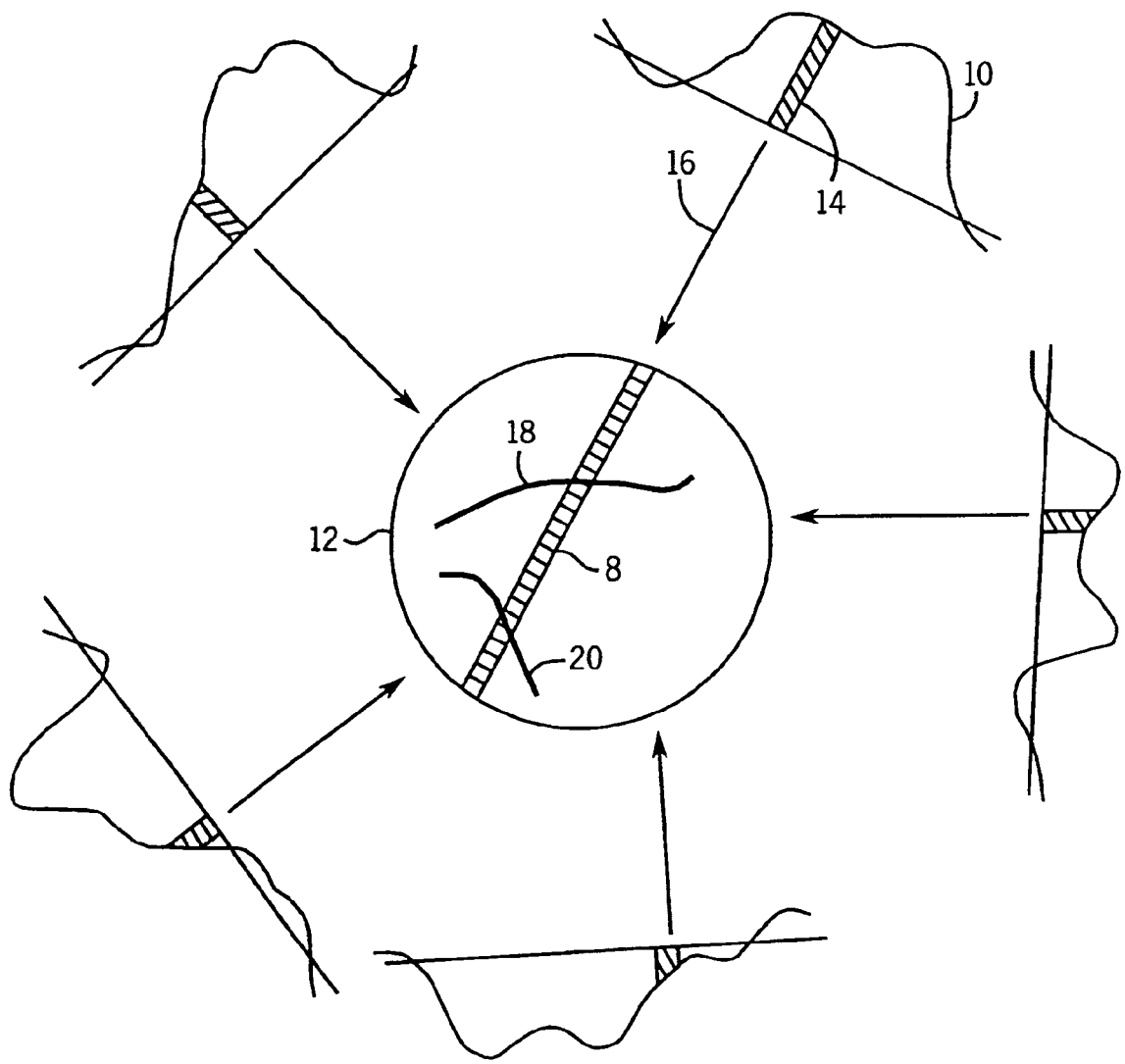
FIG. 4 is a pictorial 2D representation of the same step using a highly constrained backprojection.
Figure 5:
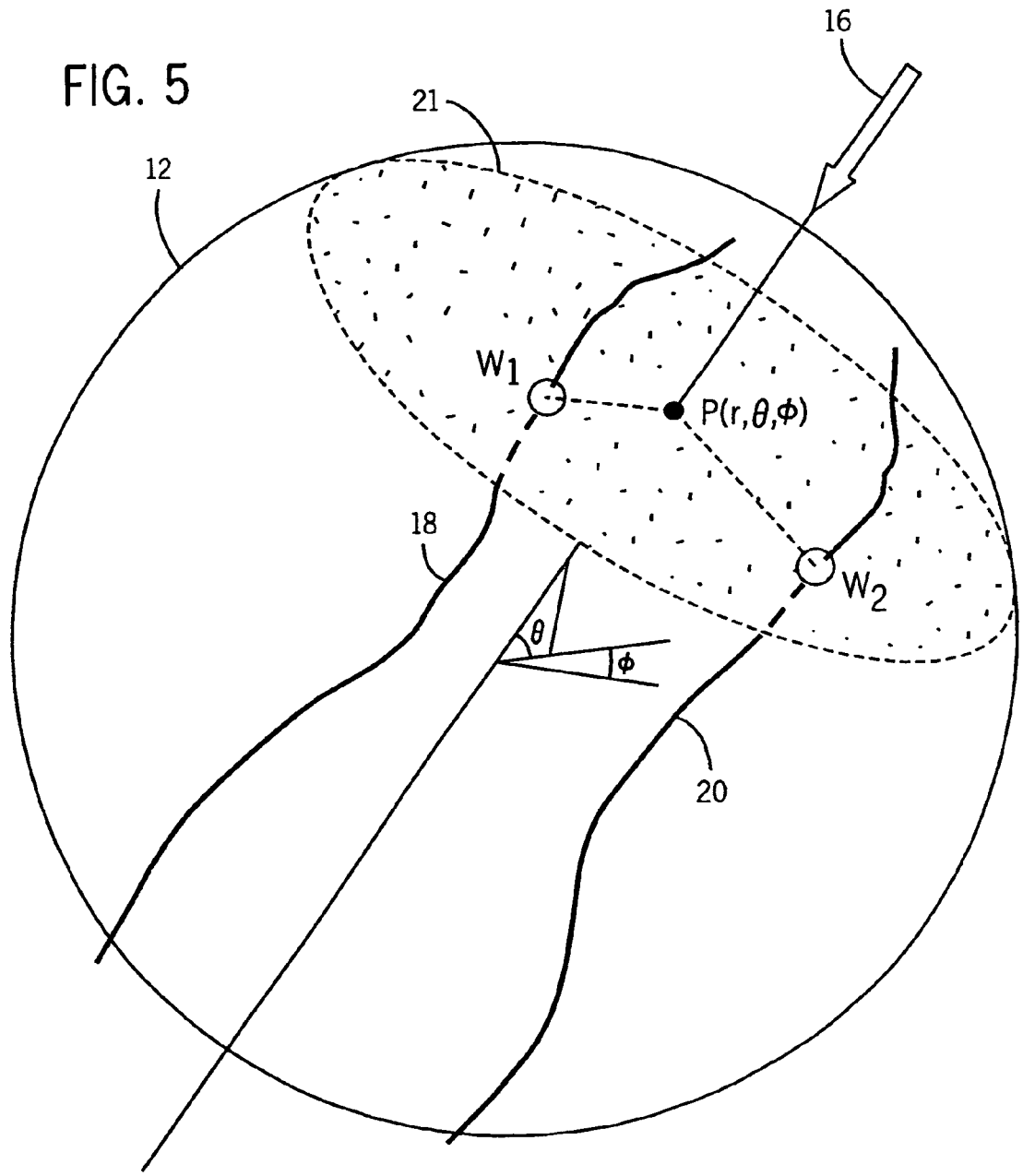
FIG. 5 is a pictorial representation of a 3D implementation of the same step using a highly constrained backprojection.
Figure 10:
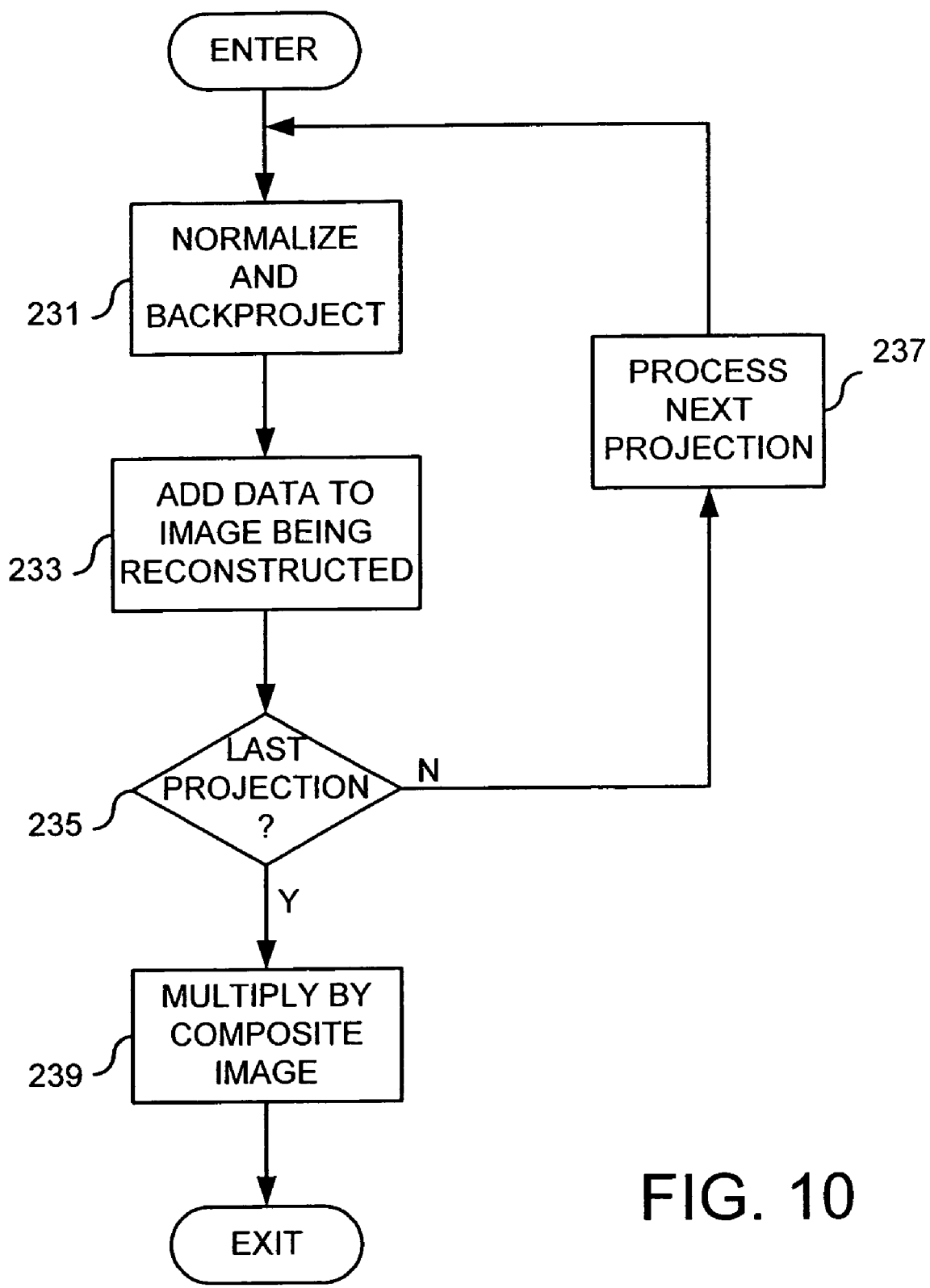
FIG. 10 is a flow chart of the steps used to reconstruct an image in the method of FIG. 9.

Referring particularly to FIG. 10, each of the |I| and |Q| component image frames 325 and 329 is reconstructed using their respective |I| and |Q| projection data sets 323 and 327 and their corresponding |I| or |Q| composite image 319 and 321. This highly constrained backprojection reconstruction is described above with respect to equation (2) and shown pictorially in FIG. 4. More particularly, each |I| and |Q| component projection P is normalized as indicated at process block 231. Each component projection P is normalized by dividing it by the projection $P_c$ in its corresponding composite image at the same view angle. The normalized projection $P/P_c$ is then backprojected into the FOV. This is a standard backprojection, but with no filtering.

As indicated at process block 233 the resulting backprojected values are added to the |I| or |Q| image frame being reconstructed and a test is made at decision block 235 to determine if all the projection views for the current image frame have been backprojected. If not, the next projection view in the current Iii or |Q| image frame is backprojected as indicated at process block 237.

When all the projection views have been backprojected and summed for an |I| or |Q| image frame, the summed image frame is multiplied by its corresponding |I| or |Q| composite image 319 and 321. This is a matrix multiplication in which the pixel value in the |I| or |Q| image frame is multiplied by the value of the corresponding pixel in the respective |I| or |Q| composite image. It should be apparent that other methods for performing this highly constrained image frame reconstruction may be used as described in co-pending U.S. patent application Ser. No. 11/482,372, filed on Jul. 7, 2006 and entitled "Highly Constrained Image Reconstruction Method", and which is incorporated herein by reference.

While |I| and |Q| component images have been produced for each image frame, the sign information has been lost and we do not know the sign (±) of the |I| and |Q| component at each image pixel. This sign information is restored by producing I and Q sign maps 333 as indicated in FIG. 9 at process block 215. The I and Q sign maps are produced by examining the signs of the I and Q components in the undersampled complex difference images 309. As indicated above, these are poor quality images due to the undersampling, but they are good enough to indicate the sign at each image pixel.

As indicated at process block 217, this sign information is then restored to the |I| and |Q| image frames 325 and 329. This is accomplished by multiplying the |I| component image frames 325 by their corresponding I sign maps 333 and multiplying the |Q| component image frames 329 by their corresponding Q sign maps 333. As indicated at process block 219, the signed I and Q components for each image frame are then combined to form a complex difference image ($\vec{CD}$) 335.

The above procedure is repeated for each motion encoded direction. In the preferred embodiment motion encoding is employed in all three gradient directions and after |CD| images 331 and $\vec{CD}$ images 335 are produced for all the directions as determined at decision block 221, the system branches to calculate n velocity images at process block 223.

In order to calculate the spin velocity the phase difference $\phi_v$ between the $+M_1$ motion encoded image and the $-M_1$ motion encoded image must be calculated. This is illustrated in FIG. 7 where the angle $\phi_B$ is the background phase produced by factors other than spin motion.

The law of cosines is used to compute the phase $\phi_v$ for each image pixel:

$$\phi_v = \cos^{-1}(-|CD|^2 + |-M_1|^2 + |+M_1|^2 / 2 \cdot |+M_1| \cdot |-M_1|) \quad (6)$$

Figure 12:
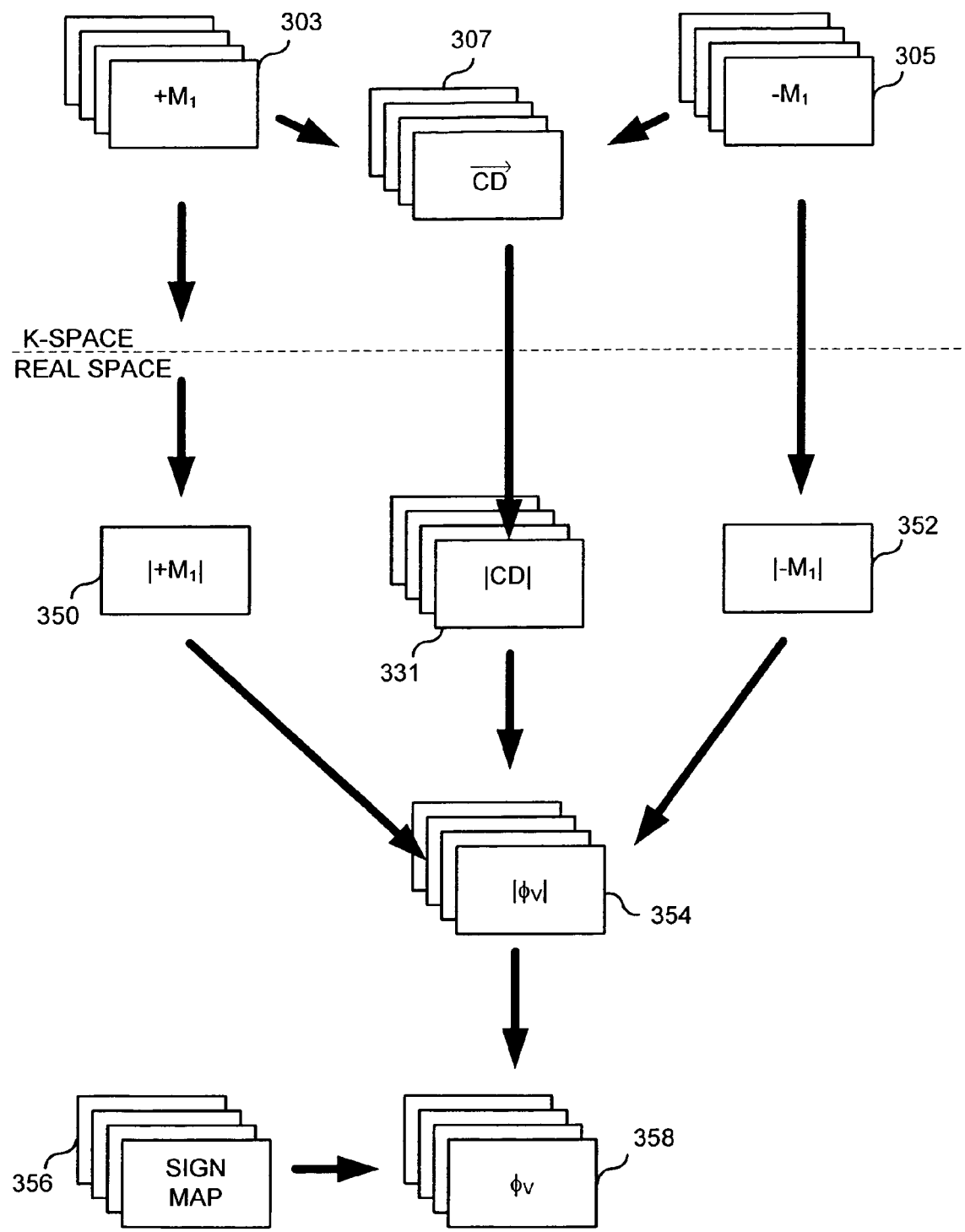
FIG. 12 is a flow chart of the steps used to produce a phase image.

As shown in FIG. 12 the complex difference values |CD| are calculated as described above for the |CD| images 331, but the $+M_1$ and $-M_1$ magnitude images must be separately calculated. This can be done in a number of ways, but in the preferred embodiment all the interleaved $+M_1$ projection views 303 for the single direction are used to reconstruct a single $|+M_1|$ image 350, and all the interleaved $-M_1$ projection views 305 for the single direction are used to reconstruct a single $|-M_1|$ image 352. These are conventional filtered backprojection reconstructions since there are sufficient views to provide quality images. The magnitudes at each $|+M_1|$ and $|-M_1|$ image pixel is calculated from the resulting complex I and Q values.

Equation (6) is used to produce each of n phase images $|\phi_v|$ 354 using the corresponding n |CD| images 331 and the two magnitude images $|+M_1|$ 350 and $|-M_1|$ 352. The phase images 354 do not contain sign information, however, and this must be added. To do this a sign map 356 is produced from the under sampled complex difference image $\vec{CD}$ 309 which indicates at each of its pixels the sign +1 or –1 of the phase difference. The absolute value phase images 354 are multiplied by their corresponding sign maps 356 to produce phase images $\phi_v$ 358.

The phase image $\phi_v$ 358 is calculated for each motion encoding direction (x, y, and z in the preferred embodiment) and the velocity components $V_x$, $V_y$, and $V_z$ are calculated therefrom as follows:

$$V = VENC^* \phi_v / \pi/2$$

where: VENC=spin velocity which produces a phase shift $\phi_v$ of $\pi/2$ radians with the chosen gradient first moment $M_1$.

These three velocity components are then combined as indicated above in equation (5) to produce n corresponding total velocity image frames.

Although velocity encoding along all three gradient axes is employed in the preferred embodiment, there are clinical situations in which velocity encoding along only one or two gradient axes will suffice. For coronary artery measurements, one may, for example, acquire a 2D image in a slice perpendicular to the flow. Only one velocity axis is encoded. This shortens both the acquisition and image reconstruction steps. In this case, the velocity encoding gradient $G_M$ is an oblique angle corresponding to the direction of the coronary artery, and it is produced by generating the $G_M$ gradient waveform simultaneously along two or three gradient axes $G_x$, $G_y$ or $G_z$ in the pulse sequence of FIG. 6.

The present invention may also be used to produce a series of phase contrast MRA images. In such an application either a 2D or 3D pulse sequence may be used and a series of images are acquired in which motion encoding is applied along only one axis. Two images are acquired with either $+M_1$ and $-M_1$ motion encoding or $+M_1$ and $M_1$=0 motion encoding. In PCMRA the phase $\phi_v$ at each reconstructed image pixel is displayed directly rather than computing a spin velocity, and as a result, the above-described procedure can be simplified. If a 3D image is acquired, the highly constrained backprojection described above with reference to FIG. 10 and Equation (2) is performed as depicted in FIG. 10 with the three-dimensional Equation (2a) discussed above.

In the above-described preferred embodiment the composite images are formed by combining information derived from projections acquired during the entire scan. While this provides maximum SNR in-the reconstructed image frames, changes in velocity that may occur during the scan may not be a clearly shown in the series of n velocity images. Thus, where changes occur during the dynamic scan one can reduce the number of projections used to form a composite image to a window surrounding the acquisition of the current image frame being reconstructed. For example, a window comprised of the current image frame plus the projections acquired in the two image frames before and after the current image frame may be used to form a composite image. This window moves for each image frame being processed, and thus a different composite image is formed for each image frame in the series.

In the preferred embodiment the background phase caused by factors other than spin motion is detected by subtracting two signals produced with bipolar gradients of opposite polarity, or first moment $M_1$. An alternative way to accomplish the same result is to acquire a second projection view with the same pulse sequence, but with no motion encoding (i.e.,. $M_1$=0). The difference between the resulting two acquired signals will reveal the undesired background phase shifts but the SNR of the resulting velocity images is reduced. This embodiment has the time advantage that a single reference acquisition can be used with one, two or three different motion direction encodings. Thus, instead of six acquisitions as described above in the preferred embodiment, only four are required at each projection angle. In addition, a "4-point balanced/hammard" encoding scheme may also be used.

Another alternative embodiment of the invention employs a different method for preserving the sign information during the image reconstruction process. Rather than reconstructing absolute value (i.e., speed) images and merging them with direction information embodied in the sign map as described above, separate positive speed images and negative speed images can be reconstructed and combined to form velocity images. In this case, instead of forming absolute |I| and |Q| component image frames at process block 201, positive I and Q and negative I and Q component image frames are formed. All of these are then separately processed as described above and then combined after the highly constrained backprojection steps.

The present invention is particularly applicable to motion encoded acquisitions in which spin motion is reflected in the phase difference information and the correct phase information must be preserved during the highly constrained backprojection process. There are other applications in which phase difference information or phase information must be preserved. The present invention applies to these situations as well. For example, there are applications where motion encoded pulse sequences are not employed to acquire the two sets of projection views that are subtracted to form the complex difference data set 307. The invention is employed on this difference data set as described above to reconstruct a corresponding complex difference image. Also, there are applications where an acquired set of complex projection views are used to reconstruct an image using the highly constrained reconstruction method, and the phase information is to be preserved. In such applications the above described procedure is employed on the sets of complex projection views and corresponding complex images are reconstructed from which accurate phase information may be extracted.

The invention claimed is:

1. A method for producing an image of a subject positioned in a field of view (FOV) of a magnetic resonance imaging system, the steps comprising:
   a) acquiring with the MRI system a set of projection views of the subject positioned in the FOV using a pulse sequence with a motion sensitizing gradient directed along a first direction, the set of projection views forming a first undersampled image data set;
   b) acquiring with the MRI system a second set of projection views of the subject positioned in the FOV using the pulse sequence with a different motion sensitizing gradient directed along the first direction, the second set of projection views forming a second undersampled image data set;
   c) repeating steps a) and b) a plurality of times to acquire additional first and second sets of projection views, wherein the projection views in the additional sets of projection views are interleaved;
   d) producing a plurality of complex difference projection data sets by subtracting I and Q components in corresponding projection views in each of said first and second undersampled image data sets;
   e) reconstructing a plurality of undersampled complex difference images from the corresponding plurality of complex difference projection data sets;
   f) producing a plurality of I component projection data sets from the plurality of complex difference images;
   g) producing an I component composite image from projection data in a plurality of said I component projection data sets;
   h) producing a plurality of Q component projection data sets from the plurality of complex difference images;
   i) producing a Q component composite image from projection data in a plurality of said Q component projection data sets;
   j) reconstructing an I image from an I component projection data set by:
      j)i) backprojecting the projection views in the I component projection data set into the FOV and weighting the value backprojected into each I image pixel by the normalized value of the corresponding pixel in the I component composite image; and
      j)ii) summing the backprojected values for each I image pixel;
   k) reconstructing a Q image from a Q component projection data set by:
      k)i) backprojecting the projection views in the Q component projection data set into the FOV and weighting the value backprojected into each Q image pixel by the normalized value of the corresponding pixel in the Q component composite image; and
      k)ii) summing the backprojected values for each Q image pixel; and
   l) combining the reconstructed I image with the reconstructed Q image to form a complex difference image.

2. The method as recited in claim 1 in which each I and Q image pixel backprojected value $S_n$ is calculated in steps j)i) and k)i) as $$S_n = (P \times C_n) / \sum_{n=1}^{N} C_n$$

where: P=the I or Q component projection view value being backprojected;
$C_n$=corresponding pixel value in the I or Q component composite image;
$S_n$=the value of the $n^{th}$ pixel along the backprojection path in the I or Q image being reconstructed; and
N=total number of pixels along the backprojection path.

3. The method as recited in claim 1 in which the FOV is three-dimensional, a three-dimensional complex difference image is produced, and the I and Q images reconstructed in steps j) and k) are:

$I(x, y, z) = \Sigma(P(r, \theta, \phi) * C(x, y, z)_{(r,\theta,\phi)}/P_c(r, \theta, \phi)$ $Q(x, y, z) = \Sigma(P(r, \theta, \phi) * C(x, y, z)_{(r,\theta,\phi)}/P_c(r, \theta, \phi)$ where the summation ($\Sigma$) is over all projection views used to reconstruct the I or Q image; $I_{(x,y,z)}$ is the image value at pixel location x, y, z in the reconstructed I image; $Q_{(x,y,z)}$ is the image value at pixel x,y,z in the reconstructed Q image; $P_{(r,\theta,\phi)}$ is the value back projected from the I or Q component projection view acquired at view angle $\theta, \phi$; $C_{(x,y,z)}$ is the I or Q component composite image value at the pixel location x, y, z; and $P_c(r,\theta,\phi)$ is the projection profile value from the I or Q component composite image at the view angle $\theta, \phi$.

4. The method as recited in claim 1 in which additional complex difference images are produced by repeating steps j), k) and l) with different ones of the I component projection data sets and Q component projection data sets.

5. The method as recited in claim 1 which includes producing a phase image from the complex difference image.

6. The method as recited in claim 5 which includes:
calculating a sign map from an undersampled complex difference image; and
multiplying the phase image by the sign map.

7. The method as recited in claim 1 which includes producing a velocity image from the complex difference image.

8. The method as recited in claim 1 which includes:
m) repeating steps a) through l) using a motion encoding gradient in steps a), b) and c) directed along a second direction to produce a second complex difference image;
n) repeating steps a) through l) using a motion encoding gradient in steps a), b) and c) directed along a third direction to produce a third complex difference image; and
o) producing a velocity image using the three complex difference images.

9. A method for producing an image of a subject positioned in a field of view (FOV) of a magnetic resonance imaging system, the steps comprising:
a) acquiring with the MRI system a set of projection views of the subject positioned in the FOV using a pulse sequence, the set of projection views forming a first undersampled image data set;
b) acquiring with the MRI system a second set of projection views of the subject positioned in the FOV using the pulse sequence, the second set of projection views forming a second undersampled image data set;
c) repeating steps a) and b) a plurality of times to acquire additional first and second sets of projection views, wherein the projection views in the additional sets of projection views are interleaved;
d) producing a plurality of complex difference projection data sets by subtracting I and Q components in corresponding projection views in each of said first and second undersampled image data sets;
e) reconstructing a plurality of undersampled complex difference images from the corresponding plurality of complex difference projection data sets;
f) producing a plurality of I component projection data sets from the plurality of complex difference images;
g) producing an I component composite image from projection data in a plurality of said I component projection data sets;
h) producing a plurality of Q component projection data sets from the plurality of complex difference images;
i) producing a Q component composite image from projection data in a plurality of said Q component projection data sets;
j) reconstructing an I image from an I component projection data set by:
j)i) backprojecting the projection views in the I component projection data set into the FOV and weighting the value backprojected into each I image pixel by the normalized value of the corresponding pixel in the I component composite image; and
j)ii) summing the backprojected values for each I image pixel;
k) reconstructing a Q image from a Q component projection data set by:
k)i) backprojecting the projection views in the Q component projection data set into the FOV and weighting the value backprojected into each Q image pixel by the normalized value of the corresponding pixel in the Q component composite image; and
k)ii) summing the backprojected values for each Q image pixel; and l) combining the reconstructed I image with the reconstructed Q image to form a complex difference image.

10. The method as recited in claim 9 in which each I and Q image pixel backprojected value $S_n$ is calculated in steps j)i) and k)i) as $$S_n = (P \times C_n) \Big/ \sum_{n=1}^{N} C_n$$

where: P=the I or Q component projection view value being backprojected;
$C_n$=corresponding pixel value in the I or Q component composite image;
$S_n$=the value of the $n^{th}$ pixel along the backprojection path in the I or Q image being reconstructed; and
N=total number of pixels along the backprojection path.

11. The method as recited in claim 9 in which the FOV is three-dimensional, a three-dimensional complex difference image is produced, and the I and Q images reconstructed in steps j) and k) are:

$I(x, y, z) = \Sigma(P(r, \theta, \phi) * C(x, y, z)_{(r,\theta,\phi)}/P_c(r, \theta, \phi)$ $Q(x, y, z) = \Sigma(P(r, \theta, \phi) * C(x, y, z)_{(r,\theta,\phi)}/P_c(r, \theta, \phi)$ where the summation ($\Sigma$) is over all projection views used to reconstruct the I or Q image; $I_{(x,y,z)}$ is the image value at pixel location x, y, z in the reconstructed I image; $Q_{(x,y,z)}$ is the image value at pixel x,y,z in the reconstructed Q image; $P_{(r,\theta,\phi)}$ is the value back projected from the I or Q component projection view acquired at view angle $\theta$, $\phi$; $C_{(x,y,z)}$ is the I or Q component composite image value at the pixel location x, y, z; and $P_c(r,\theta,\phi)$ is the projection profile value from the I or Q component composite image at the view angle $\theta$, $\phi$.

12. The method as recited in claim 9 in which additional complex difference images are produced by repeating steps j), k) and l) with different ones of the I component projection data sets and Q component projection data sets.

13. The method as recited in claim 9 which includes producing a phase image is produced from the complex difference image.

14. The method as recited in claim 13 which includes:
calculating a sign map from an undersampled complex difference image; and
multiplying the phase image by the sign map.

15. A method for producing an image of a subject positioned in a field of view (FOV) of a magnetic resonance imaging system, the steps comprising:
a) acquiring with the MRI system a set of projection views of the subject positioned in the FOV using a pulse sequence, the set of projection views forming a first undersampled image data set;
b) repeating step a) a plurality of times to acquire additional first set of projection views, wherein the projection views in the additional sets of projection views are interleaved;
c) reconstructing a plurality of undersampled images from the corresponding plurality of projection data sets;
d) producing a plurality of I component projection data sets from the plurality of undersampled images;
e) producing an I component composite image from projection data in a plurality of said I component projection data sets;
f) producing a plurality of Q component projection data sets from the plurality of undersampled images;

g) producing a Q component composite image from projection data in a plurality of said Q component projection data sets;

h) reconstructing an I image from an I component projection data set by:

h)i) backprojecting the projection views in the I component projection data set into the FOV and weighting the value backprojected into each I image pixel by the normalized value of the corresponding pixel in the I component composite image; and h)ii) summing the backprojected values for each I image pixel;

i) reconstructing a Q image from a Q component projection data set by:

i)i) backprojecting the projection views in the Q component projection data set into the FOV and weighting the value backprojected into each Q image pixel by the normalized value of the corresponding pixel in the Q component composite image; and i)ii) summing the backprojected values for each Q image pixel; and j) combining the reconstructed I image with the reconstructed Q image to form a complex image.

16. The method as recited in claim 15 in which each I and Q image pixel backprojected value $S_n$ is calculated in steps h)i) and i)i) as $$S_n = (P \times C_n) / \sum_{n=1}^{N} C_n$$

where: P=the I or Q component projection view value being backprojected;

$C_n$=corresponding pixel value in the I or Q component composite image;

$S_n$=the value of the $n^{th}$ pixel along the backprojection path in the I or Q image being reconstructed; and N=total number of pixels along the backprojection path.

17. The method as recited in claim 15 in which the FOV is three-dimensional, a three-dimensional complex difference image is produced, and the I and Q images reconstructed in steps h) and i) are:

$$I(x, y, z) = \Sigma(P(r, \theta, \phi) * C(x, y, z)_{(r,\theta,\phi)} / P_c(r, \theta, \phi)$$

$$Q(x, y, z) = \Sigma(P(r, \theta, \phi) * C(x, y, z)_{(r,\theta,\phi)} / P_c(r, \theta, \phi)$$

where the summation ($\Sigma$) is over all projection views used to reconstruct the I or Q image; $I_{(x,y,z)}$ is the image value at pixel location x, y, z in the reconstructed I image; $Q_{(x,y,z)}$ is the image value at pixel x,y,z in the reconstructed Q image; $P_{(r,\theta,\phi)}$ is the value back projected from the I or Q component projection view acquired at view angle $\theta, \phi$; $C_{(x,y,z)}$ is the I or Q component composite image value at the pixel location x, y, z; and $P_c(r,\theta,\phi)$ is the projection profile value from the I or Q component composite image at the view angle $\theta, \phi$.

18. The method as recited in claim 15 which includes producing a phase image from the complex image.

19. The method as recited in claim 18 which includes:

calculating a sign map from an undersampled image; and multiplying the phase image by the sign map.

* * * * *

UNITED STATES PATENT AND TRADEMARK OFFICE
CERTIFICATE OF CORRECTION

PATENT NO.       : 7,711,166 B2
APPLICATION NO.  : 11/518036
DATED            : May 4, 2010
INVENTOR(S)      : Charles A Mistretta It is certified that error appears in the above-identified patent and that said Letters Patent is hereby corrected as shown below:

Column 4, line 39, Eq. (2a), "$I(x,y,z)=\sum (P(r,\theta,\phi) * C(x,y,z)_{(r,\theta,\phi)} / P_c(r,\theta,\phi)$"

should be -- $I(x,y,z)=\sum (P(r,\theta,\phi) * C(x,y,z)_{(r,\theta,\phi)} / P_c(r,\theta,\phi))$ --.

Column 14, Claim 3, lines 50 & 52, $$I(x, y, z) = \sum (P(r, \theta, \phi) * C(x, y, z)_{(r,\theta,\phi)} / P_c(r, \theta, \phi)$$

" $Q(x, y, z) = \sum (P(r, \theta, \phi) * C(x, y, z)_{(r,\theta,\phi)} / P_c(r, \theta, \phi)$ " should be $$I(x, y, z) = \sum (P(r, \theta, \phi) * C(x, y, z)_{(r,\theta,\phi)} / P_c(r, \theta, \phi))$$

$$Q(x, y, z) = \sum (P(r, \theta, \phi) * C(x, y, z)_{(r,\theta,\phi)} / P_c(r, \theta, \phi))$$ --.

Column 16, Claim 14, lines 24 & 26, $$I(x, y, z) = \sum (P(r, \theta, \phi) * C(x, y, z)_{(r,\theta,\phi)} / P_c(r, \theta, \phi)$$

" $Q(x, y, z) = \sum (P(r, \theta, \phi) * C(x, y, z)_{(r,\theta,\phi)} / P_c(r, \theta, \phi)$ " should be $$I(x, y, z) = \sum (P(r, \theta, \phi) * C(x, y, z)_{(r,\theta,\phi)} / P_c(r, \theta, \phi))$$

$$Q(x, y, z) = \sum (P(r, \theta, \phi) * C(x, y, z)_{(r,\theta,\phi)} / P_c(r, \theta, \phi))$$ --.

Column 18, Claim 17, lines 13 & 15, $$I(x, y, z) = \sum (P(r, \theta, \phi) * C(x, y, z)_{(r,\theta,\phi)} / P_c(r, \theta, \phi)$$

" $Q(x, y, z) = \sum (P(r, \theta, \phi) * C(x, y, z)_{(r,\theta,\phi)} / P_c(r, \theta, \phi)$ " should be Signed and Sealed this
Twentieth Day of September, 2011

David J. Kappos
*Director of the United States Patent and Trademark Office*

CERTIFICATE OF CORRECTION (continued)

U.S. Pat. No. 7,711,166 B2

$$I(x, y, z) = \sum (P(r, \theta, \phi) * C(x, y, z)_{(r,\theta,\phi)} / P_c(r, \theta, \phi)\underline{)}$$

$$Q(x, y, z) = \sum (P(r, \theta, \phi) * C(x, y, z)_{(r,\theta,\phi)} / P_c(r, \theta, \phi)\underline{)}$$

-- --.